United States Patent
Pagnoux et al.

(10) Patent No.: US 8,665,436 B2
(45) Date of Patent: Mar. 4, 2014

(54) DEVICE AND METHOD FOR DETERMINING A PIECE OF POLARISATION INFORMATION AND POLARIMETRIC IMAGING DEVICE

(75) Inventors: Dominique Pagnoux, Limoges (FR); Frédéric Louradour, Eymoutiers (FR); Jérôme Desroches, Limoges (FR); Alain Barthelemy, Limoges (FR); Julien Brevier, Saint-Junien (FR)

(73) Assignee: Centre National de la Recherche Scientifique—CNRS, Paris (FR)

( * ) Notice: Subject to any disclaimer, the term of this patent is extended or adjusted under 35 U.S.C. 154(b) by 187 days.

(21) Appl. No.: 13/144,311

(22) PCT Filed: Jan. 15, 2010

(86) PCT No.: PCT/FR2010/050064
§ 371 (c)(1),
(2), (4) Date: Jul. 13, 2011

(87) PCT Pub. No.: WO2010/082000
PCT Pub. Date: Jul. 22, 2010

(65) Prior Publication Data
US 2011/0273711 A1 Nov. 10, 2011

(30) Foreign Application Priority Data

Jan. 15, 2009 (FR) ...................................... 09 50236
Jan. 28, 2009 (FR) ...................................... 09 50535

(51) Int. Cl.
*G01J 4/00* (2006.01)
(52) U.S. Cl.
USPC ......................................................... 356/367
(58) Field of Classification Search
USPC ......................................................... 356/367
See application file for complete search history.

(56) References Cited

U.S. PATENT DOCUMENTS 4,626,679 A 12/1986 Kuwayama et al.
(Continued)

FOREIGN PATENT DOCUMENTS

WO WO 9853272 11/1998

OTHER PUBLICATIONS

Search Report from related PCT Application No. PCT/FR2010/050064; Report dated May 17, 2010.
(Continued)

*Primary Examiner* — Gregory J Toatley
*Assistant Examiner* — Hina F Ayub
(74) *Attorney, Agent, or Firm* — Miller, Matthias & Hull LLP

(57) ABSTRACT

The invention relates to a method and to a device for determining a piece of polarisation information on a measurement point of a target sample, the device comprising: —a light source capable of emitting a rectilinearly polarised light beam in a predefined direction, the light beam being intended to be reflected by the measurement point of the target sample; —a unit for computing the piece of polarisation information on the measurement point using the beam reflected by the target sample; -a waveguide for guiding the incident beam towards the target sample and the reflected beam towards the computing means; and —a unit for rotating the polarisation, capable of rotating two orthogonal polarimetric components of the incident beam exiting the waveguide and two orthogonal polarimetric components of the reflected beam before passing through the waveguide.

13 Claims, 4 Drawing Sheets

(56) References Cited

U.S. PATENT DOCUMENTS

| | | | |
|---|---|---|---|
| 5,389,783 A * | 2/1995 | Shionoya et al. | 250/234 |
| 5,887,009 A | 3/1999 | Mandella et al. | |
| 6,292,287 B1 | 9/2001 | Fujinoki | |
| 2010/0128268 A1 * | 5/2010 | Dainty et al. | 356/367 |

OTHER PUBLICATIONS

Nielsen P M F et al: "Polarization-Sensitive Scanned Fiber Confocal Microscope"; Optical Engineering, Soc. of Photo-Optical; Instrumentation Engineers, Bellingham, vol. 35, No. 11, Nov. 1, 1996, pp. 3084-3091, XP000638602; ISSN: 0091-3286; p. 3084-p. 3085; figure 1.

* cited by examiner

DEVICE AND METHOD FOR DETERMINING A PIECE OF POLARISATION INFORMATION AND POLARIMETRIC IMAGING DEVICE

CROSS-REFERENCE TO RELATED APPLICATIONS

This application is a U.S. national stage filing of International Patent Application No. PCT/FR2010/050064 filed on Jan. 15, 2010, which claims priority under the Paris Convention to French Patent Application No. 09 50236, filed on Jan. 15, 2009 and French Patent Application No. 09 50535 filed on Jan. 28, 2009.

FIELD OF THE DISCLOSURE

The invention relates to a device and a method for determining a piece of polarisation information for a point of a target sample, as well as a polarimetric imaging device.

BACKGROUND OF THE DISCLOSURE

In particular, the invention relates to a determining device comprising:
- a light source capable of emitting a rectilinearly polarised light beam in a predefined direction, the light beam being intended to be reflected by the measurement point of the target sample,
- a means for calculating the polarisation information for the measurement point from the beam reflected by the target sample,
- at least one waveguide for guiding the incident beam towards the target sample and the reflected beam towards the calculation means, the waveguide being a polarisation-maintaining optical fiber having a proper optical axis parallel to the predefined direction.

U.S. Pat. No. 7,289,211 describes an example of such a determining device.

Such a device for determining polarisation information provides information on the micro or nanostructure of target samples, and on their texture at the surface or slightly beneath the surface. This polarisation information can be, for example, the degree of polarisation of the beam returned by the target sample. This information is primarily used in the medical field for diagnosis, and in the field of microelectronics for characterizing single-layer or multi-layer thin films or for analyzing complex surfaces.

Generally, the polarisation information is obtained by reflecting a polarised light beam on a target sample. Polarisation information for the target sample can be determined by analyzing the polarisation of the reflected beam.

This technique requires the use of a light beam with direct line of sight to and unencumbered space around the target area. It is not possible to measure polarisation information from an object situated in an area difficult to access, inside a cavity, or in an obscuring environment.

SUMMARY OF THE DISCLOSURE

One goal of the invention is to overcome this disadvantage and propose a device for determining a piece of polarisation information which allows, among other things, analyzing target samples not accessible by a light beam with direct line of sight.

For this purpose, one object of the invention is the determining device mentioned above, comprising:

- a polarisation rotation means for rotating two orthogonal polarimetric components $E_{\parallel}^I$, $E_{\perp}^I$ of the incident beam after passage through the waveguide, and two orthogonal polarimetric components $E_{\parallel}^R$, $E_{\perp}^R$ of the reflected beam before passage through the waveguide, with the polarimetric component $E_{\perp}^I$ of the incident beam perpendicular to the predefined direction being zero,
- and the rotation means comprising at least one proper optical axis which is orientable around an axis of rotation, said axis of rotation being perpendicular to the proper optical axis and the predefined direction; the calculation means being capable of calculating a piece of polarisation information based on the reflected beam measured for at least three different orientations of the proper optical axis of the rotation means; said polarisation information being the orientation of the proper axes and the phase shift induced by the birefringence of the target sample.

In particular, the invention enables the analysis of biological tissue structures such as collagen, in vivo, in situ, with no need for biopsy.

Another object of the invention is a polarimetric imaging device for generating a polarimetric image of a target sample, said imaging device comprising:
- a device for determining a piece of polarisation information according to one of the embodiments previously described, said device being capable of determining multiple pieces of polarisation information,
- a unit for constructing a polarimetric image representative of the polarisation information from measurement points of the target sample, each characteristic of a pixel of the image representing the polarisation information for a measurement point of the target sample.

A last object of the invention is a method for determining a piece of polarisation information, comprising the following steps:
a) a rectilinearly polarised incident light beam is emitted in a predefined direction,
b) the incident beam is guided towards the measurement point of the target sample with the aid of a waveguide, said waveguide being a polarisation-maintaining optical fiber having a proper optical axis parallel to the predefined direction,
c) two orthogonal polarimetric components $E_{\parallel}^I$, $E_{\perp}^I$ of the incident beam are rotated after passage through the waveguide, the polarimetric component $E_{\perp}^I$ of the incident beam perpendicular to the predefined direction being zero,
d) the incident beam is reflected at the measurement point of the target sample,
e) two orthogonal polarimetric components $E_{\parallel}^R$, $E_{\perp}^R$ of the reflected beam are rotated before passage through the waveguide,
f) the reflected beam is guided towards a calculation means by the same waveguide, and
g) the polarisation information is calculated for the measurement point of the target sample, based on the reflected beam recovered at the exit from the waveguide,
steps a) to f) constituting a measurement phase; the measurement phase being performed at least three times for different angles of rotation of the polarimetric component $E_{\parallel}^F$ of the incident beam; the polarisation information for the measurement point being calculated based on the reflected beam measured during said at least three measurement phases; said polarisation information comprising the orientation of the proper axes and the phase shift induced by the birefringence of the target sample.

BRIEF DESCRIPTION OF THE DRAWINGS

The invention will be better understood by referring to the following description, provided solely as an example, and to the attached drawings in which.

In the different figures, the same references are used to denote identical or similar elements.

DETAILED DESCRIPTION OF THE DISCLOSURE

Figure 1:
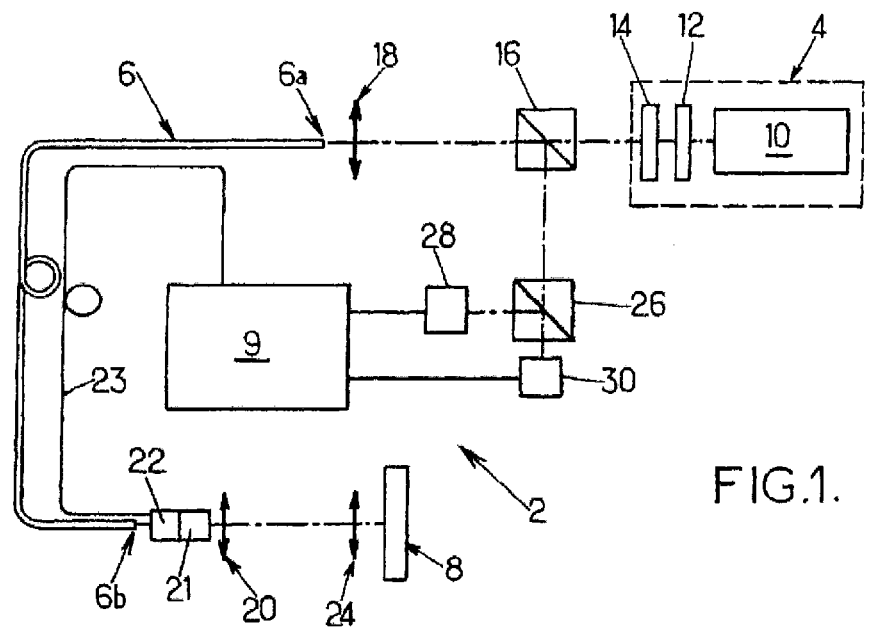
FIG. 1 is a schematic view of the determining device of the invention.

In FIG. 1, the determining device 2 comprises a monochromatic light source 4 for emitting an incident light beam, a waveguide 6 to be traversed by an incident beam and a beam reflected by the target sample 8, and a calculation means 9 for calculating the polarisation information based on the reflected beam recovered at the exit from the waveguide 6.

In the rest of the description, the light beam is referred to as the "incident beam" for the entire path from the source 4 to the target sample 8, and as the "reflected beam" for the entire path from the target sample 8 to the calculation means 9.

In the rest of the description, the terms "upstream" and "downstream" are defined relative to the direction of the light beam.

Figure 2:
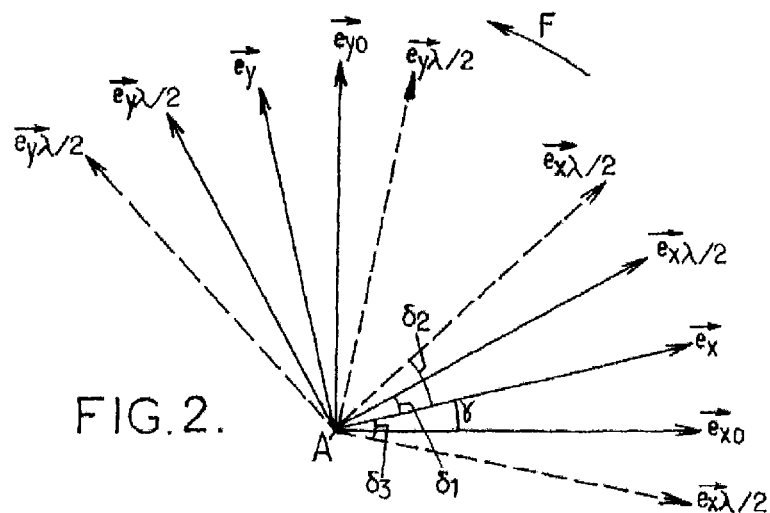
FIG. 2 is schematic representation of the orientations of the proper axes of the rotation means, proper axes of the waveguide, and proper axes of the target sample.

The angles of rotation are defined algebraically in this description relative to a trigonometric direction illustrated by the arrow F in FIG. 2.

The light source 4 is capable of emitting a rectilinearly polarised incident light beam in a predefined direction $\vec{e}_x$.

This light source 4 consists, for example, of a laser diode 10, a polariser 12, and a half-wave plate 14. The polariser 12 and the half-wave plate 14 are placed downstream from the laser diode if considering the direction of the incident beam. They are traversed by the beam emitted by the laser diode 10. The light source may include a device intended to protect it from external reflections.

The determining device 2 comprises, between the light source 4 and the waveguide 6, a beam splitter cube 16 as well as a system 18 for focusing the incident beam in the waveguide 6.

The cube 16 is polarisation neutral. It only affects the intensity of the beam coming from the light source and directed towards the waveguide 6. It is able to modify the direction of the reflected beam in order to direct it towards the calculation means 9.

The focus system 18 consists, for example, of a microscope objective or a convergent lens having a focal plane positioned at the entrance to the waveguide 6.

The waveguide 6 guides the incident beam onto the target sample 8, particularly when the target sample is positioned within a cavity or recess or even in the human body, where it cannot be reached by direct transmission of a light beam. It has one end 6a called the proximal end, situated near the light source 4 and calculation means 9, and another end 6b called the distal end, intended to be placed near the target sample 8.

The waveguide 6 consists of a single-mode optical fiber at the wavelength of the beam emitted by the light source 4.

This optical fiber is, for example, a polarisation-maintaining optical fiber having one of its proper axes parallel to the direction of polarisation $\vec{e}_x$ of the light source 4. The polarimetric component $E_\parallel^I$ of the incident beam is therefore not disrupted during its passage through the waveguide 6.

If considering the direction of the incident beam, the determining device 2 comprises, between the distal end 6b and the target sample 8, a polarisation rotation means 21, a first optical system 20 having the focal plane positioned at the opening in the distal end of the waveguide 6, and a second optical system 24 having the focal plane positioned at the target sample 8.

The rotation means 21 comprises a phase retarder having two proper optical axes denoted $$\vec{e}_{x_{\lambda/2}} \text{ and } \vec{e}_{y_{\lambda/2}}.$$

This phase retarder consists, for example, of a half-wave plate. For medical applications, this rotation means 21 is miniaturized.

The determining device 2 additionally comprises a driving means 22 for rotationally driving the proper axes $$\vec{e}_{x_{\lambda/2}}, \vec{e}_{y_{\lambda/2}}$$

around an axis of rotation A, axis A being perpendicular to the optical axis $$\vec{e}_{x_{\lambda/2}}$$

and to the direction of polarisation $\vec{e}_x$.

The driving means 22 consists, for example of an actuator. It is controlled by the calculation means 9 in order to pivot the proper axes $$\vec{e}_{x_{\lambda/2}} \text{ and } \vec{e}_{y_{\lambda/2}}$$

by at least three known angles $\delta_1, \delta_2, \delta_3$. For this purpose, the driving means 22 is connected to the calculation means 9 by an electric wire 23.

The rotation means 21 and the driving means 22 are assembled between the distal end 6b and the target sample 8. In particular, they can be attached to the distal end 6b of the waveguide.

In the invention, the calculation means 9 determined a piece of polarisation information based on the reflected beam, for at least three different orientations of the proper axes $$\vec{e}_{x_{\lambda/2}}, \vec{e}_{y_{\lambda/2}}$$

of the rotation means 21.

For better comprehension of the invention, FIG. 2 illustrates an example orientation of proper optical axes $\vec{e}_x, \vec{e}_y$ of the waveguide (the vector $\vec{e}_x$ also represents the orientation of the polarisation of the light source 4), an example orientation of proper axes $\vec{e}_{x0}$, $\vec{e}_{y0}$ of the target sample, as well as three example orientations of proper axes $$\vec{e}_{x_{\lambda/2}}, \vec{e}_{y_{\lambda/2}}$$

of the rotation means 21. The orientations illustrated in FIG. 2 are example orientations. They in no way reflect the actual orientations of the various proper axes.

FIG. 2 also represents the angle γ defined between a proper axis $\vec{e}_{x0}$ of the target sample and the direction of polarisation $\vec{e}_x$, and the angles $\delta_1$, $\delta_2$, $\delta_3$ defined between the proper axis $$\vec{e}_{x_{\lambda/2}}$$

of the rotation means 21 and the direction of polarisation $\vec{e}_x$ for three different orientations of the proper axis $$\vec{e}_{x_{\lambda/2}}$$

of the rotation means 21.

In other words, $$\gamma = (\vec{e}_x, \vec{e}_{x0});$$

for a first orientation of the proper axis $$\vec{e}_{x_{\lambda/2}} \delta_1 = (\vec{e}_x, \vec{e}_{x_{\lambda/2}});$$

for a second orientation of the proper axis $$\vec{e}_{x_{\lambda/2}} \delta_2 = (\vec{e}_x, \vec{e}_{x_{\lambda/2}});$$

for a third orientation of the proper axis $$\vec{e}_{x_{\lambda/2}} \delta_2 = (\vec{e}_x, \vec{e}_{x_{\lambda/2}}).$$

The rotation means 21 rotate two polarimetric components $E_\|^I$, $E_\perp^I$ of the incident beam in the direction of rotation F of an angle $2\delta_1$ to perform a first measurement of the reflected beam, by an angle $2\delta_2$ to perform a second measurement of the reflected beam, and by an angle $2\delta_3$ to perform a third measurement of the reflected beam.

In the embodiment of the invention in which the waveguide is a polarisation-maintaining optical fiber having a proper optical axis parallel to the predefined direction $\vec{e}_x$, the polarimetric component $E_\perp^F$ perpendicular to the predefined direction $\vec{e}_x$ is zero.

The first optical system 20 collimates the incident beam. The second optical system 24 focuses the incident beam on the measurement point of the target sample.

The incident beam is reflected by the measurement point of the target sample 8. One of the polarisation components of the incident beam is phase shifted by a value θ during this reflection. The phase shift θ is characteristic of the birefringence of the target sample 8.

After reflection from the target sample 8, the reflected beam is collimated by the second optical system 24, and is focused by the first optical system 20 at the entrance to the distal part 6b of the waveguide.

The rotation means 21 then rotates the two orthogonal polarimetric components $E_\|^R$, $E_\perp^R$ of the reflected beam, one by an angle of $2(\gamma+\delta_\perp i)$ and the other by an angle of $\pi - 2(\gamma+\delta_i)$ in the direction opposite the direction of rotation F, $\delta_i$ being the $i^{th}$ orientation of the proper axis $$\vec{e}_{x_{\lambda/2}}.$$

The angles $2(\gamma+\delta_\perp i)$ and $\pi - 2(\gamma+\delta_i)$ are defined with a polarimetric component $E_\|^R$ parallel to the proper axis $\vec{e}_{x0}$ of the target sample 8 and a polarimetric component $E_\perp^R$ perpendicular to this proper axis $\vec{e}_{x0}$.

The waveguide 6 guides the reflected beam towards the focus system 18. As the waveguide is polarisation-maintaining, the power ratio for the polarimetric components $E_\|^R$ and $E_\perp^R$ of the reflected beam is not modified during the passage through the waveguide.

The determining device 2 additionally comprises a polarisation splitter cube 26 and two photodetectors 28, 30 connected to the calculation means 9.

The cube 26 splits out a polarimetric component $E_\|^F$ oriented in the direction of polarisation $\vec{e}_x$ of the light source 4, and a polarimetric component $E_\perp^F$ perpendicular to it.

The parallel polarimetric component $E_\|^F$ and the orthogonal polarimetric component $E_\perp^F$ of the reflected beam are respectively directed towards the photodetector 28 and the photodetector 30. The photodetectors 28, 30 each deliver a photocurrent, referred to hereinafter as an electric signal, to the calculation means 9.

In the invention, the calculation means 9 calculates the angle γ between the proper axis $\vec{e}_{x0}$ of the target sample and the direction of polarisation $\vec{e}_x$, as well as the phase shift θ induced by the target sample.

For this purpose, the calculation means 9 is capable of calculating the following ratios:

$$\frac{P_{\perp 2}}{p_{\perp 1}} = \left[\frac{\sin 2(\gamma - 2\delta_2)}{\sin 2(\gamma - 2\delta_1)}\right]^2 \quad (1a)$$

$$\frac{P_{\perp 3}}{P_{\perp 1}} = \left[\frac{\sin 2(\gamma - 2\delta_3)}{\sin 2(\gamma - 2\delta_1)}\right]^2 \quad (1b)$$

in which:

$\delta_i$ is the $i^{th}$ angle defined between the proper axis $$\vec{e}_{x_{\lambda/2}}$$

of the rotation means 21 and the direction of polarisation $\vec{e}_x$, $P_{\perp i}$ is the normalized power representative of the polarimetric component $E_\perp^F$ perpendicular to the direction of polarisation $\vec{e}_x$, measured when the proper axis $$\vec{e}_{x\lambda/2}$$

of the rotation means 21 has an $i^{th}$ angle $\delta_i$ relative to the direction of polarisation $\vec{e}_x$, and γ is the angle defined between the proper axis $\vec{e}_{x0}$ of the target sample and the direction of polarisation $\vec{e}_x$;
where the normalized power $$P_{//i} = \frac{P^*_{//i}}{P^*_{//i} + P^*_{\perp i}}$$

and the normalized power $$P_{\perp i} = \frac{P^*_{\perp i}}{P^*_{//i} + P^*_{\perp i}}$$

in which $P_{\perp i}^*$ is the power measured by the photodetector 30 and $P_{//i}^*$ is the power measured by the photodetector 28.

Thus the calculation means 9 is able to calculate the angle γ based on the normalized powers $P_{\perp 1}$, $P_{\perp 2}$, $P_{\perp 3}$ representative of the perpendicular polarimetric components $E_\perp^F$ measured for the orientations $\delta_1, \delta_2, \delta_3$ of the proper axes of the rotation means.

In a variation, this angle γ may also be calculated based on the ratio between the normalized powers $P_{//1}, P_{//2}, P_{//3}$ representative of the parallel polarimetric components $E_{//}^F$ measured for the orientations $\delta_1, \delta_2, \delta_3$ of the proper axes of the rotation means.

Knowing the angle γ, the calculation means 9 calculates the phase shift θ based on the following equation:

$$\cos\theta = \frac{P_{//1} - \cos^4\gamma - \sin^4\gamma}{2\cos^2\gamma\sin^2\gamma} \quad (2)$$

in which:

$P_{//1}$, is the normalized power representative of the polarimetric component $E_{//}^F$ parallel to the direction of polarization $\vec{e}_x$, measured when the proper axis $$\vec{e}_{x\lambda/2}$$

of the rotation means 21 has the same angle $\delta_i$ relative to the direction of polarisation $\vec{e}_x$;

θ is the phase shift induced by the birefringence of the target sample during reflection; and γ is the angle defined between the proper axis $\vec{e}_{x0}$ of the target sample and the direction of polarisation $\vec{e}_x$.

Note that equations (1a), (1b), and (2) were obtained from expressions of the normalized power $P_{//i}$ of the polarimetric component $E_{//}^F$ of the reflected beam parallel to the direction of polarisation $\vec{e}_x$ for an $i^{th}$ angle of the rotation means 21, and the normalized power $P_{\perp i}$ representative of the polarimetric component $E_\perp^F$ of the reflected beam perpendicular to the direction of polarisation $\vec{e}_x$ for an $i^{th}$ angle of the rotation means 21.

$$P_{//i} \propto \cos^4\gamma_i + \sin^4\gamma_i + 2\cos^2\gamma_i \sin^2\gamma_i \cos\theta$$

$$P_{\perp i} \propto 2\cos^2\gamma_i + \sin^2\gamma_i(1-\cos\theta)$$

Figure 3:
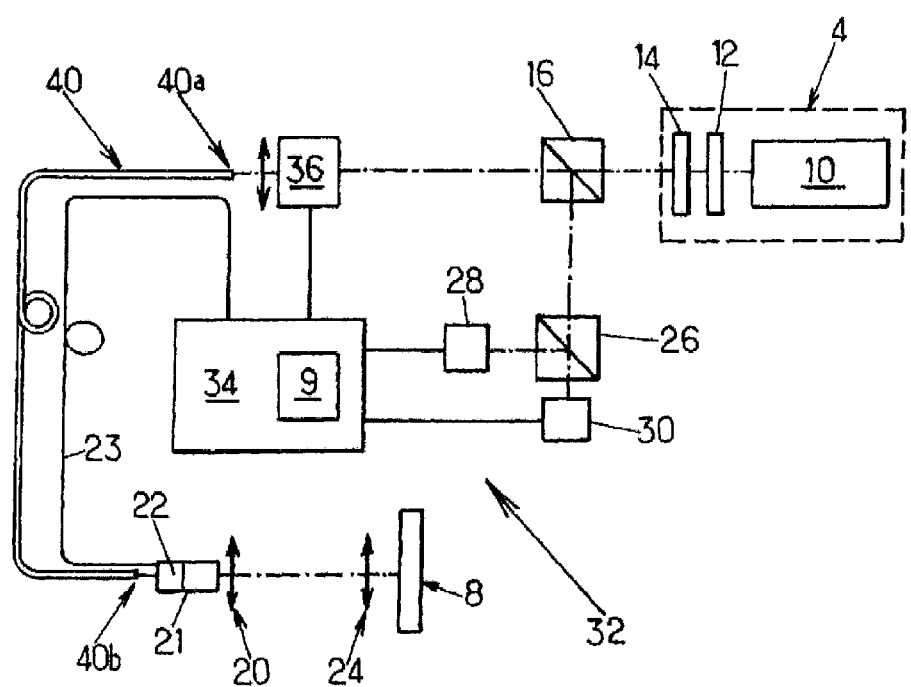
FIG. 3 is a schematic view of a polarimetric imaging device in a second embodiment of the invention.

With reference to FIG. 3, the polarimetric imaging device 32 of the invention is based on a device for determining a piece of polarisation information, as described above, equipped with a polarimetric image construction unit 34 and a scanning system 36.

However, the waveguide 6 of the determining device 2 is replaced with several waveguides 40, or with a multi-core optical fiber having proper axes that are parallel to one another.

The construction unit 34 receives polarisation information coming from several measurement points in the target sample 8, and constructs a polarimetric image from these. Each grayscale or each chrominance of a pixel in the image represents the information associated with a measurement point of the target sample.

The image construction unit 34 is synchronized with the scanning system 36 for this purpose.

The scanning system 36 is capable of directing the incident beam towards several measurement points of the target sample 8.

The scanning system 36 is placed upstream from the waveguide if considering the direction in which the incident beam travels. It is able to direct the incident beam towards each waveguide in turn, such that the beam successively illuminates several measurement points of the target sample 8.

The scanning system sequentially processes the reflected beam when it is received. The construction unit 34 is synchronized with the scanning system 36 so that it can assign each item of polarisation information calculated by the calculation unit 9 to a corresponding position on the target sample 8.

It consists, for example, of two mirrors which oscillate, one on a vertical axis, the other on a horizontal axis, at a frequency corresponding to the frequency at which an image is constructed by the construction unit 34. It is connected to the construction unit 34.

The construction unit 34 generates a polarimetric image representative of the orientation γ of the proper axis $\vec{e}_{x0}$ of the target sample 8, a polarimetric image representative of the phase shift θ, or an image showing both the phase shift θ and the orientation γ of a proper axis of the target sample.

In a variation, the waveguide comprises a single optical fiber and the scanning system 36 is placed downstream from the waveguide if considering the direction of travel of the incident beam. In particular, it is placed between the distal end 6b of the waveguide and the target sample 8. In this case, the scanning system 36 is capable of directing the incident beam towards several measurement points of the target sample.

In a variation, the optical fiber or fibers used are polarisation-maintaining multi-mode optical fibers.

In a variation, the monochromatic light source is replaced by a polychromatic source 44 consisting, for example, of a superluminescent diode. In this case, the polarimetric imaging device 32 is able to generate wavelength information and polarisation response information for the target sample.

Figure 4:
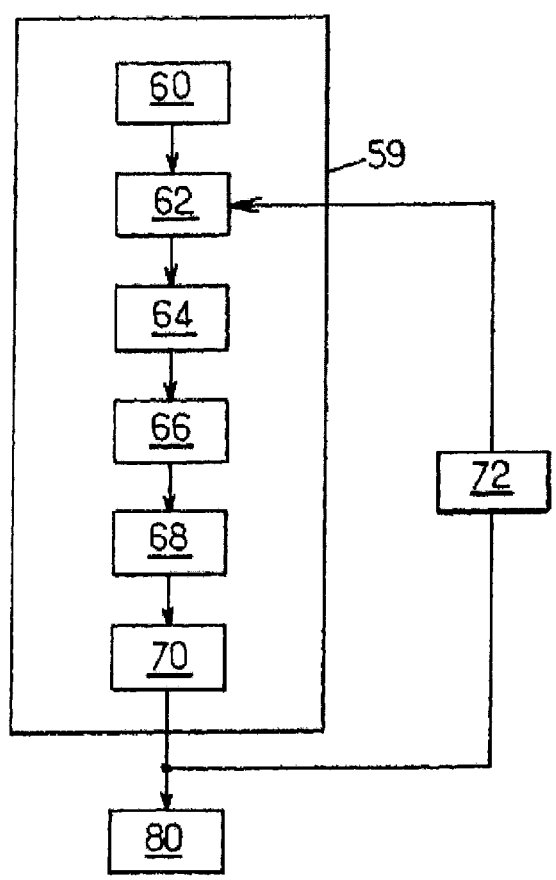
FIG. 4 is a diagram illustrating the steps in the method of the invention.
Figure 5:
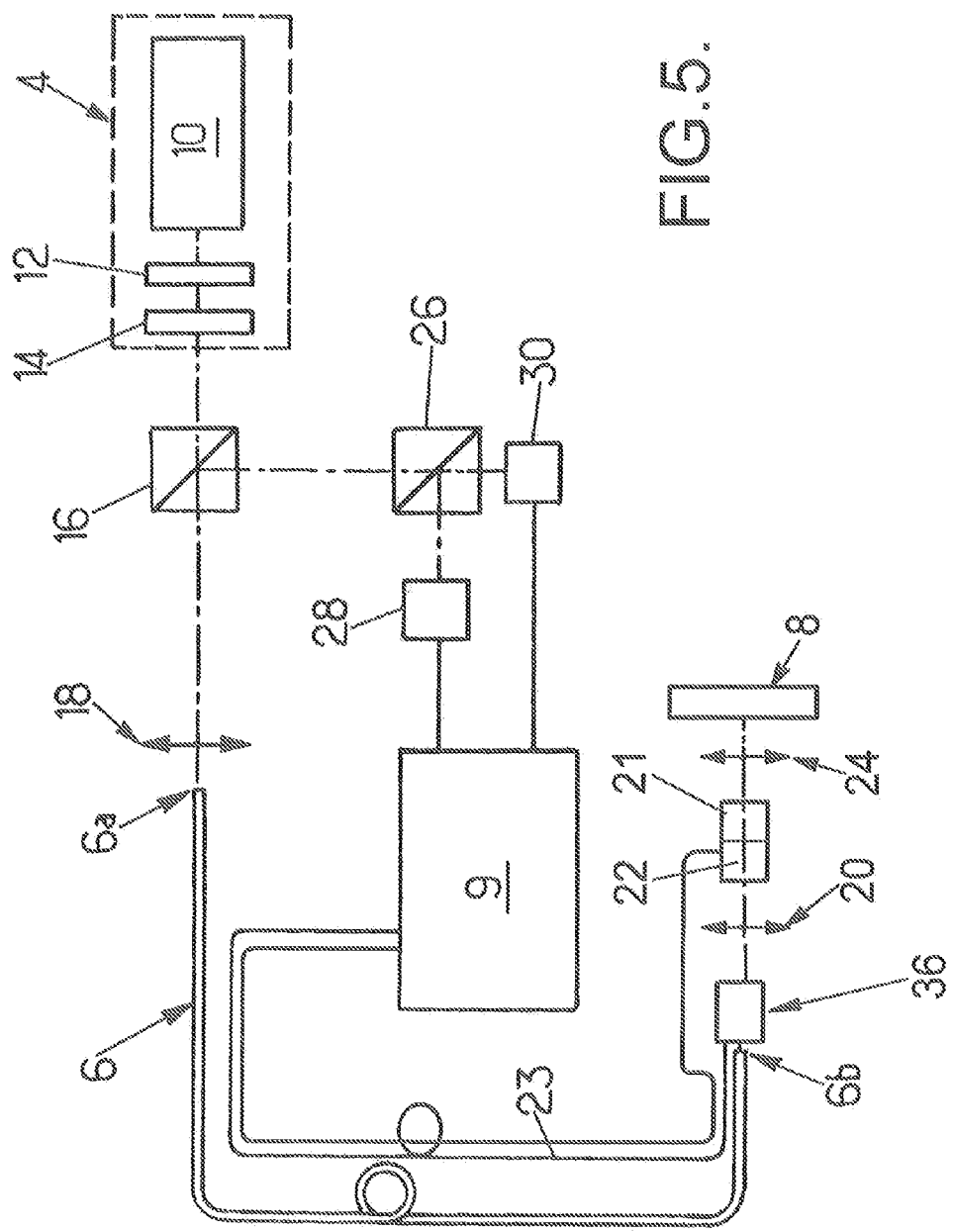
FIG. 5 is a schematic representation of a scanning system placed downstream from a waveguide.

The invention also concerns a method for determining a piece of polarisation information. The method illustrated in FIG. 4 comprises a measurement phase 59 followed by a calculation phase 80.

The measurement phase 59 begins with a step 60 in which a rectilinearly polarised incident light beam $E_\parallel^I$ is emitted.

During a step 62, the incident beam is guided towards the measurement point of the target sample with the aid of the waveguide 6.

During a step 64, the polarimetric components $E_\parallel^I$, $E_\perp^I$ of the incident beam are rotated by the rotation means 21 by an angle of $2\delta_1$ and $\pi+2\delta_1$ respectively, defined algebraically relative to the direction of rotation F.

In the embodiment of the invention in which the waveguide is a polarisation-maintaining optical fiber having a proper optical axis parallel to the predefined direction $\vec{e}_x$, the polarimetric component $E_\perp^F$ perpendicular to the predefined direction $\vec{e}_x$ is zero.

During a step 66, the incident beam is reflected at the measurement point of the target sample.

During a step 68, two orthogonal polarimetric components $E_\parallel^F$, $E_\perp^F$ of the reflected beam are rotated, one by an angle of $2(\gamma-\delta_1 1)$ the other by an angle of $\pi-2(\gamma-\delta_1)$, in a direction opposite the direction of rotation F. Then the reflected beam is injected into the waveguide 6 by the optical system 20.

During a step 70, the reflected beam is guided towards the calculation unit 9 by the same waveguide 6.

The splitter cube 26 splits out a polarimetric component $E_\parallel^F$ oriented in the predefined direction $\vec{e}_x$ which it sends towards the photodetector 28, and a polarimetric component $E_\perp^F$ oriented perpendicularly to the predefined direction $\vec{e}_x$ which it sends towards the photodetector 30. Each photodetector 28, 30 delivers an electric signal to the calculation means 9 which stores this information.

During a step 72, the driving means 22 rotates the proper axis $$\vec{e}_{x\lambda/2}$$

of the rotation means 21 around the axis of rotation A such that it forms an angle $\delta_2$ relative to the direction of polarisation $\vec{e}_x$.

Then steps 62 to 70 are repeated for this new orientation $\delta_2$.

In particular, during step 64, two polarimetric components of the incident beam are rotated by the rotation means 21 by an angle of $2\delta_2$ defined algebraically relative to the direction of rotation F. In the embodiment of the invention in which the waveguide is a polarisation-maintaining optical fiber having a proper optical axis parallel to the predefined direction $\vec{e}_x$, the polarimetric component $E_\perp^F$ perpendicular to the predefined direction $\vec{e}_x$ is zero.

During step 68, the orthogonal polarimetric components $E_\parallel^F$, $E_\perp^F$ of the reflected beam are rotated in a direction opposite the direction of rotation F, one by an angle of $2(\gamma-\delta_2)$, the other by an angle of $\pi-2(\gamma-\delta_2)$.

Lastly, the driving means 22 rotates the proper axis $$\vec{e}_{x\lambda/2}$$

of the rotation means 21 around the axis of rotation A such that it forms an angle $\delta_3$ relative to the direction of polarisation $\vec{e}_x$.

Then steps 62 to 70 are repeated for this new orientation $\delta_3$.

During the phase 80, the calculation means 9 calculates the angle $\gamma$ defined between the proper axis $\vec{e}_{x0}$ of the target sample and the direction of polarisation $\vec{e}_x$, based on the ratios (1a) and (1b) of the electric signals delivered during the steps 70, and angles $\delta_1$, $\delta_2$, and $\delta_3$.

Then the calculation unit 9 determines the phase shift $\theta$ based on equation (2).

For example, the angles $\delta_1$, $\delta_2$, and $\delta_3$ are respectively equal to 0 degrees, $-\delta$ degrees, and $+\delta$ degrees where $\delta$ is not equal to 45 degrees.

The determinations of $\gamma$ and $\theta$ via the measures described above assume that the target sample has only a linear birefringence, meaning the target sample is not depolarising, and that it has no circular birefringence or dichroism.

In a variation, the reflected beam is guided towards the calculation means by another optical fiber having a proper axis parallel to the proper axis of the optical fiber carrying the incident beam.

The invention claimed is:

1. A device for determining at least one piece of polarisation information for a measurement point of a target sample, said device comprising:
    a light source configured to emit a rectilinearly polarised light beam in a predefined direction, the light beam being intended to be reflected by the measurement point of the target sample,
    a calculation unit configured to calculate the polarisation information for the measurement point from the beam reflected by the target sample,
    at least one waveguide configured to guide the incident beam towards the target sample and the reflected beam towards the calculation means, said waveguide being a polarisation-maintaining optical fiber having a main optical axis parallel to the predefined direction,
    wherein the device additionally comprises a half-wave plate configured to rotate two orthogonal polarimetric components $E_\parallel^I$, $E_\perp^I$ of the incident beam after passage through the waveguide, and two orthogonal polarimetric components $E_\parallel^R$, $E_\perp^R$ of the reflected beam before passage through the waveguide, the polarimetric component $E_\perp^I$ of the incident beam perpendicular to the predefined direction being zero,
    and wherein the half wave plate comprises at least one main optical axis which is orientable around an axis of rotation, said axis of rotation being perpendicular to the main optical axis and the predefined direction; the calculation unit being configured to calculate a piece of polarisation information based on the reflected beam measured from only three different orientations of the main optical axis of the half wave plate; said polarisation information being the orientation of the main axes and the phase shift induced by the birefringence of the target sample.

2. A device according to claim 1, wherein the calculation unit is configured to calculate a piece of polarisation information based on at least one reflected beam measured when the main optical axis of the polarisation means is parallel to the predefined direction.

3. A device according to claim 1, wherein said device comprising a driving means for rotationally driving the main optical axis of the phase retarder.

4. A device according to claim 1, wherein the waveguide comprises a proximal end intended to be placed next to the light source, and a distal end intended to be placed next to the target sample, the half wave plate being placed between the target sample and the distal end of the waveguide.

5. A device according to claim 1, wherein the reflected beam comprises a polarimetric component $E_\|^F$ oriented in the predefined direction and a polarimetric component $E\perp^F$ perpendicular to the predefined direction, said device comprising photodetectors configured to measure the reflected beam which deliver two electric signals, one representative of the polarimetric component $E_\|^F$ of the reflected beam oriented in the predefined direction, and the other representative of the polarimetric component $E_\perp^F$ perpendicular to the predefined direction;

and wherein the calculation unit is capable of calculating at least one piece of polarisation information based on electric signals delivered during the measurement of at least three reflected beams for different orientations of the main optical axis of the half wave plate.

6. A device according to claim 1, wherein the light source is monochromatic.

7. A device according to claim 1, wherein the waveguide is either a single-mode optical fiber at the or at each wavelength of the beam emitted by the light source, or a polarisation-maintaining multi-mode optical fiber.

8. A polarimetric imaging device able to generate a polarimetric image of a target sample, said imaging device comprising:
a device for determining a piece of polarisation information according to claim 1, said device being capable of determining multiple pieces of polarisation information,
an image construction unit configured to construct a polarimetric image representative of the polarisation information from measurement points of the target sample, each characteristic of a pixel of the image representing the polarisation information for a measurement point of the target sample.

9. A polarimetric imaging device according to claim 8, comprising multiple waveguides and two one-dimensionally oscillating mirrors placed upstream from said waveguides when considering the direction of the incident beam, said mirrors being configured to direct the incident beam towards several measurement points of the target sample, said mirrors being controlled by the image construction unit and being synchronized with it.

10. A polarimetric imaging device according to claim 8, comprising a single waveguide and two one-dimensionally oscillating mirrors placed downstream from the waveguide when considering the direction of the incident beam, said mirrors being configured to direct the incident beam towards several measurement points of the target sample, said mirrors being controlled by the image construction unit and being synchronized with it.

11. A method for determining at least one piece of polarisation information for a measurement point of a target sample, said method comprising the following steps:
a) a rectilinearly polarised incident light beam is emitted in a predefined direction,
b) the incident beam is guided towards the measurement point of the target sample with the aid of a waveguide, the waveguide being a polarisation-maintaining optical fiber having a main optical axis parallel to the predefined direction,
c) two orthogonal polarimetric components $E_\|^I$, $E_\perp^I$ of the incident beam are rotated after passage through the waveguide, the polarimetric component $E_\perp^I$ of the incident beam perpendicular to the predefined direction being zero,
d) the incident beam is reflected at the measurement point of the target sample;
e) two orthogonal polarimetric components $E_\|^R$; $E_{195}{}^R$ of the reflected beam are rotated before passage through the waveguide;
f) the reflected beam is guided towards a calculation unit by the same waveguide, and
g) the polarisation information is calculated for the measurement point of the target sample, based on the reflected beam recovered at the exit from the waveguide;
steps a) through f) constituting a measurement phase; the measurement phase being performed only three times for different angles of rotation of the polarimetric component $E_\|^F$ of the incident beam; the polarisation information for the measurement point being calculated based on the reflected beam measured during said only three measurement phases; said polarisation information comprising the orientation of the main axes and the phase shift induced by the birefringence of the target sample.

12. A method according to claim 11, wherein one of said angles of rotation of the polarimetric components $E_\Pi^{I\ and}\ E_\perp^I$ of the incident beam is zero.

13. A device according to claim 5, wherein the calculation unit is configured to calculate the phase shift induced by the birefringence of the target sample, based on the following equations:

$$\cos\theta = \frac{P_{/\!/1} - \cos^4\gamma - \sin^4\gamma}{2\cos^2\gamma\sin^2\gamma} \quad (2)$$

$$\frac{P_{\perp 2}}{p_{\perp 1}} = \left[\frac{\sin2(\gamma - 2\delta_2)}{\sin2(\gamma - 2\delta_1)}\right]^2 \quad (1a)$$

$$\frac{P_{\perp 3}}{P_{\perp 1}} = \left[\frac{\sin2(\gamma - 2\delta_3)}{\sin2(\gamma - 2\delta_1)}\right]^2 \quad (1b)$$

in which:
$P_{/\!/1}$ is a normalized power representative of the polarimetric component $E_\|^F$ parallel to the direction of polarization $\bar{e}_x$, measured when the main axis $$\vec{e}_{x_{\lambda/2}}$$

of the half wave plate has a first angle $\delta_i$ relative to the direction of polarisation $\bar{e}_x$;
θ is the phase shift induced by the birefringence of the target sample during reflection; and
γ is the angle defined between a main axis $\bar{e}_{x_n}$ of the target sample and the direction of polarisation $\bar{e}_x$;
$\delta_i$ is the $i^{th}$ angle defined between the main axis $$\vec{e}_{x_{\lambda/2}}$$

of the half wave plate and the direction of polarisation $\vec{e}_x$, $P_{\perp i}$ is the normalized power representative of the polarimetric component $E_\perp^F$ perpendicular to the direction of polarisation $\vec{e}_x$, measured when the main axis $$\vec{e}_{x_{\lambda/2}}$$

of the half wave plate has an $i^{th}$ angle $\delta$ relative to the direction of polarisation $\vec{e}_x$.

* * * * *